(12) United States Patent
Bellani

(10) Patent No.: US 6,894,167 B2
(45) Date of Patent: May 17, 2005

(54) METHOD OF PREPARATION OF (S)-N-TERT-BUTYL-1,2,3,4-TETRAHYDROISOQUINOLINE-3-CARBOXAMIDE

(75) Inventor: Pietro Bellani, Milan (IT)

(73) Assignee: Clariant Life Science Molecules (Italia) S.p.A., Milan (IT)

( * ) Notice: Subject to any disclaimer, the term of this patent is extended or adjusted under 35 U.S.C. 154(b) by 15 days.

(21) Appl. No.: 10/398,274

(22) PCT Filed: Sep. 27, 2001

(86) PCT No.: PCT/IB01/01788
§ 371 (c)(1),
(2), (4) Date: Apr. 4, 2003

(87) PCT Pub. No.: WO02/30905
PCT Pub. Date: Apr. 18, 2002

(65) Prior Publication Data
US 2004/0034056 A1 Feb. 19, 2004

(51) Int. Cl.$^7$ ............................................. C07D 421/00
(52) U.S. Cl. ...................................................... 546/162
(58) Field of Search ........................................... 546/162

(56) References Cited

U.S. PATENT DOCUMENTS

| | | | |
|---|---|---|---|
| 5,196,438 A | 3/1993 | Martin et al. ................ | 514/311 |
| 5,256,783 A | 10/1993 | Gokhale et al. ............ | 546/146 |
| 5,484,926 A | 1/1996 | Dressman et al. .......... | 546/114 |
| 5,587,481 A | 12/1996 | Allen et al. .................. | 546/146 |
| 5,952,343 A | 9/1999 | Dressman et al. .......... | 514/307 |

FOREIGN PATENT DOCUMENTS

| | | |
|---|---|---|
| EP | 0 161 102 | 11/1985 |
| EP | 0 533 000 | 3/1993 |
| EP | 0 751 128 | 1/1997 |
| WO | WO 00/00494 | 1/2000 |

OTHER PUBLICATIONS

Casreact 52:77028, "A new synthesis of cysteinyl peptides", Sheehan et. al., Journal of the American chemical Society (1958), 80, 1158–64.*

XP–000889687, Gohring, Wolfgang, et al., "Synthesis of the HIV–Proteinase Inhibitor Saquinavir: A Challenge for Process Research", Chimia, AARAU, CH, vol. 50, No. 11, 1996, pp. 532–537.

* cited by examiner

Primary Examiner—Joseph K. McKane
Assistant Examiner—Binta Robinson
(74) Attorney, Agent, or Firm—Anthony A. Bisulca

(57) ABSTRACT

A new method is described here for the synthesis of (S)-N-tert-butyl-1,2,3,4-tetrahydroiso-quinoline-3-carboxamide comprising the following steps:

a) (3S)-1,2,3,4-tetrahydroisoquinoline-3-carboxylic acid is reacted with formic acid to give the compound of formula:

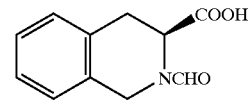

b) the compound thus obtained is reacted with tert-butylamine to give the compound of formula:

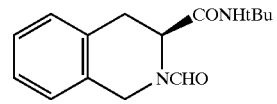

c) the compound thus obtained is then treated with acids to give the desired compound.

The method in question makes it possible to obtain (S)-N-tert-butyl-1,2,3,4-tetrahydroiso-quinoline-3-carboxamide with high yields and purity without using toxic and hazardous reagents.

14 Claims, No Drawings

METHOD OF PREPARATION OF (S)-N-TERT-BUTYL-1,2,3,4-TETRAHYDROISOQUINOLINE-3-CARBOXAMIDE

The present invention relates to a new method of preparation of (S)-N-tert-butyl-1,2,3,4-tetrahydroisoquinoline-3-carboxamide, the structural formula of which is given below,

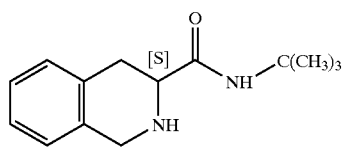

and which is a key intermediate in the preparation of compounds with high pharmacological activity, which can be used in particular in the treatment and prevention of infections caused by HIV.

In the majority of these antiviral drugs, (S)-N-tert-butyl-1,2,3,4-tetrahydroisoquinoline-3-carboxamide is not used directly as such but is hydrogenated beforehand to give N-tert-butyldecahydro-(4aS,8aS)-isoquinoline-3the structural formula of which is also given below,

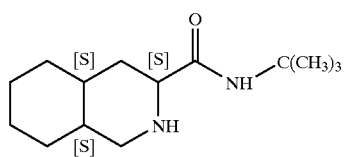

and which, after suitable substitutions on the isoquinoline nitrogen that will be obvious to a person skilled in the art, is in its turn converted to the pharmacologically active derivative.

U.S. Pat. No. 5,196,438 in fact describes pharmacologically active compounds with antiviral activity, the structural formula of which is given below

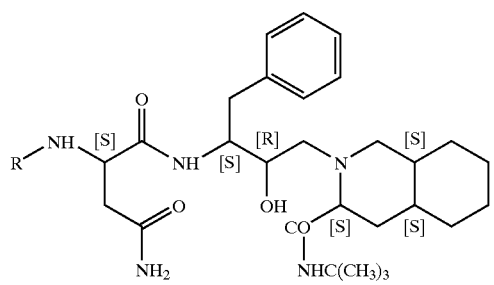

and in which the decahydroisoquinoline residue derived from N-tert-butyldecahydro(4aS,8aS)-isoquinoline-3(S)-carboxamide is immediately identifiable; among these, the derivative of most interest, and whose structural formula is given below,

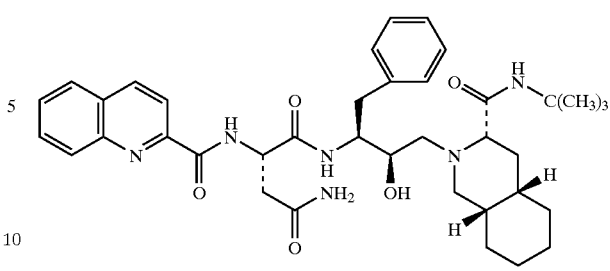

is known by the trade name Saquinavir.

Another antiviral drug of considerable importance, which also contains the decahydroiso-quinoline residue present in Saquinavir, is Nelfinavir, the structural formula of which is also given below.

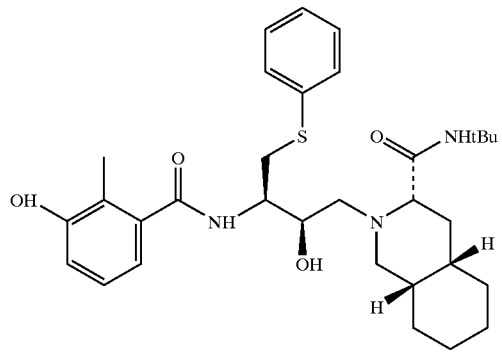

and the preparation of which is described for example in U.S. Pat. Nos. 5,484,926 and 5,952,343, the contents of which, as well as the contents of U.S. Pat. No. 5,196,438, must be regarded as an integral part of the present description.

Both Nelfinavir and Saquinavir are normally used in the form of the corresponding water-soluble salts and, in particular, of the associated mesylate salts.

European patent application EP-533000-A1 describes a process for the preparation of (S)-N-tert-butyl-1,2,3,4-tetrahydroisoquinoline-3-carboxamide in which a compound of formula IV,

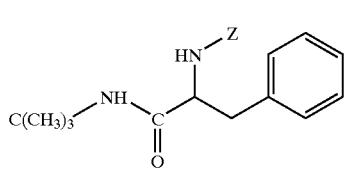

IV where Z=benzyloxycarbonyl, is reacted with formaldehyde in acetic acid in the presence of sulphuric acid to give compound V

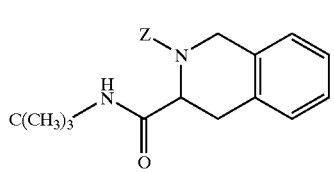

V which is then converted to the desired compound as a result of removal of the Z group. However, this method is of little industrial interest as it is characterized by mediocre yields.

U.S. Pat. No. 5,587,481, European patent application EP-751128-A1 and international patent application WO 00/00494 describe a method for the synthesis of (S)-N-tert butyl-1,2,3,4-tetrahydroisoquinoline-3-carbox in which (3S)-1,2,3,4-tetrahydroisoquinoline-3-carboxylic acid

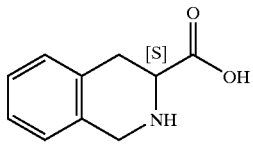

is reacted with phosgene, diphosgene or triphosgene to give the corresponding N-carboxy anhydride (NCA), shown below.

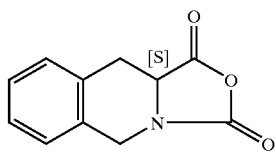

The NCA is then reacted with tert-butylamine and next it is hydrogenated to give N-tert-butyldecahydro-(4aS,8aS)-isoquinoline-3(S)-carboxamide.

The method described in U.S. Pat. No. 5,587,481, EP-751128-A1 and WO 00/00494 does, however, have substantial drawbacks, for example the use of phosgene, diphosgene and triphosgene which are toxic and highly hazardous compounds.

A method that enables (S)-N-tert-butyl-1,2,3,4-tetrahydroisoquinoline-3-carboxamide to be synthesized at high yield and with high optical purity and does not use reagents that are toxic and difficult to use, would therefore be of industrial interest.

A new method of synthesis by which the intermediate in question can be prepared at high yields and with high optical purity without the use of hazardous reagents has now been found, and constitutes the subject of the present invention; this method of synthesis is made up of the following steps:

a) compound of formula

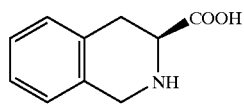

i.e. (3S)-1,2,3,4-tetrahydroisoquinoline-3-carboxylic acid, is reacted with formic acid to give the compound of formula:

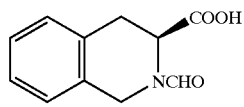

b) the compound thus obtained is reacted with tert-butylamine to give the compound of formula:

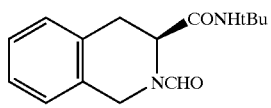

c) the compound thus obtained is then treated with acids to give (S)-N-tert-butyl-1,2,3,4-tetrahydroisoquinoline-3-carboxamide.

(S)-N-tert-Butyl-1,2,3,4-tetrahydroisoquinoline-3-carboxamide can then be hydrogenated to give N-tert-butyldecahydro-(4aS,8aS)-isoquinoline-3(S)-carboxamide according to the known methods in the prior art, for example those described in EP-533000-A1, U.S. Pat. No. 5,587,481, EP-751128-A1 and WO 00/00494, which must be regarded as an integral part of the present description.

A second subject of the invention is moreover represented by a method for the synthesis of compounds with antiviral activity and of their water-soluble salts, such as Nelfinavir and Saquinavir for example, characterized in that they comprise the synthesis steps described above. Further subjects of the invention are finally represented by the intermediates

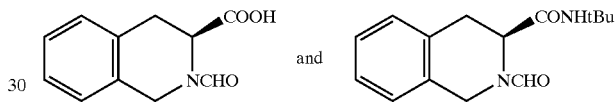

used in the present method.

Steps (a), (b) and (c), can be effected in the conditions known in the industry by similar reactions. According to the preferred embodiment of the present invention, which is not however to be regarded as limiting, step (a) is normally carried out in toluene in the presence of acetic anhydride, operating at a temperature of 30–70° C., preferably at approx. 50° C. Step (b), reaction with t-butylamine, is normally carried out in ethyl acetate, possibly in the presence of triethylamine and ethyl chloroformate, operating at a temperature between −20 and +10° C., preferably at approx. −2° C. Step (c), finally, is preferably carried out in dioxan and hydrochloric acid, normally at 36%, operating at a temperature between 10 and 40° C., preferably at approx. 25° C.

As will be clear from the examples, which must be regarded purely as illustrating but not limiting the invention, (3S)-1,2,3,4-tetrahydroisoquinoline-3-carboxylic acid, used as starting product in the present method, can be obtained by reaction of I-phenylalanine

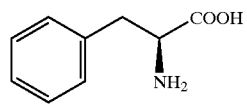

with formaldehyde (preferably in the form of paraformaldehyde), as described for example in Pictet Spengler reaction, Chem. Pharm. Bull., 31, 312, 1983, which is also regarded as an integral part of the present description.

EXAMPLE 1

Synthesis of (3S)-1,2,3,4-tetrahydroisoquinoline-3-carboxylic Acid

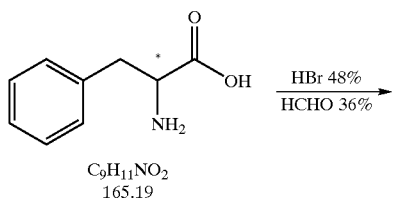

$C_9H_{11}NO_2$
165.19

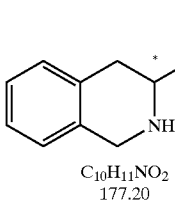

$C_{10}H_{11}NO_2$
177.20

A suitable reactor is loaded with 1.32 kg of I-phenylalanine and 1.38 kg of HBr 48%; after stirring for 30 min, 2.3 kg of formaldehyde is added at approx. 20° C.; it is heated to 65° and stirred for 9 h. It is then cooled to 0°–5° and stirred slowly for about 2 h; it is filtered on a porous diaphragm, washing with a mixture of 0.6 kg of HBr 48% and 1.8 kg of H₂O. The wet product is loaded into 5.3 kg of H₂O and the pH is adjusted to 8–9 (T <25° C.) with 1.7 kg of NaOH 30%; it is then acidified to pH 6–7 with concentrated HCl. It is cooled to 5–10° C., stirred for 1 h and filtered on a porous diaphragm, washing well with water; it is dried in a stove at approx. 70° C. under vacuum. 1.23 kg is obtained (yield 86.9% of theor.) and at purity (HPLC) of 96.00%.

EXAMPLE 2

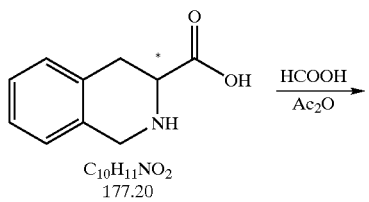

$C_{10}H_{11}NO_2$
177.20

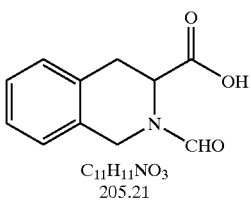

$C_{11}H_{11}NO_3$
205.21

4.5 kg of HCOOH 95–97% is loaded into a suitable reactor; it is cooled to approx. 5° C. and 1.23 kg of the product obtained in Example 1 is added slowly at <10° C.; it is stirred for 30 min and 0.86 kg of acetic anhydride is added slowly at <10° C.; then the temperature is allowed to rise to 20° C. and it is stirred for 2 h. It is distilled under vacuum at 40° C. until there is a residue, it is absorbed in 0.3 kg of ethyl acetate and then distilled until there is a residue. 3.7 kg of H₂O is added, and it is kept stirred for 30 min, allowing the product to "gin"; it is cooled to 5° C., stirred for 2 h and filtered on a diaphragm. It is then dried in a stove under vacuum at >7° C. 1.39 kg of product is obtained (yield 97.6% of theor.) with a purity (HPLC) of 97%.

EXAMPLE 2a 50 g of the product obtained in Example 1 and 250 ml of toluene (K.F. 0.06%) are loaded into a 500-ml flask at room temperature. The mixture is cooled to 0° C./5° C. and, maintaining that temperature, a mixture of formic acid 98% (19.5 g) and acetic anhydride (43.3 g), prepared by heating a mixture of the two at 50° C. for 30 min, is poured in. Upon completion of pouring, the temperature is allowed to rise to 20° C./25° C. spontaneously and, after about two hours, the mixture is concentrated under vacuum at a maximum temperature of 35° C. until there is a residue. The residue is absorbed in toluene (100 ml) and is concentrated to residue again. The operation is repeated once more. Finally, the residue is absorbed in toluene (200 ml), stirring for 30 min at 30° C. until the "ginned" product is obtained. It is cooled to 0° C./5° C. and stirred for 60 min. It is filtered and the panel is washed with toluene (50 ml, twice); it is dried under vacuum at 55° C. 54 g of product is obtained (yield 1.08 based on phenylalanine) with HPLC purity of 98.4%.

EXAMPLE 3

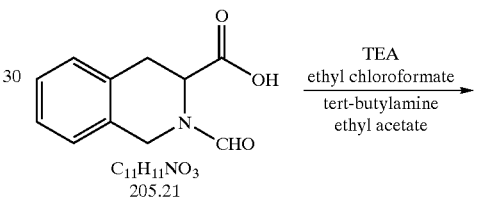

$C_{11}H_{11}NO_3$
205.21

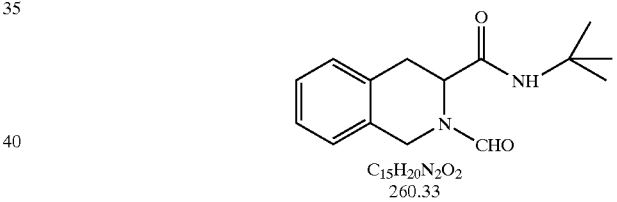

$C_{15}H_{20}N_2O_2$
260.33

A suitable reactor is loaded with 1.39 kg of the product obtained in Example 2 (or 2a) and 7.5 kg of ethyl acetate; then 0.89 kg of triethylamine is poured in slowly at 20° C.; it is stirred for 30 min at room temperature and then 2.5 kg of ethyl acetate and 1.1 kg of ethyl chloroformate are added (at −2° C.). It is stirred for 30 min and 0.74 kg of tbutylamine is poured in slowly at −2° C.; it is stirred for 30 min and a further 0.25 kg of ethyl chloroformate is added slowly at −2° C.; it is stirred for 20 min and a further 0.15 kg of t-butylamine is added slowly at −2° C.; the temperature is allowed to rise to 20° C. and it is stirred for 2 h from the end of addition. Then 2 kg of H₂O is added, it is stirred for 30 min and it is left to decant, allowing the phases to separate; 2.8 kg of H₂O with 5% of NaHCO₃ is added to the organic phase, it is stirred for 30 min, leaving it to decant and allowing the phases to separate. 2 kg of H₂O is added, it is stirred again for 30 min, and it is left to decant, allowing the phases to separate; it is distilled under vacuum at 40° C. until there is an oily residue of a red-orange Golour (HPLC purity approx. 90% 95%).

EXAMPLE 4

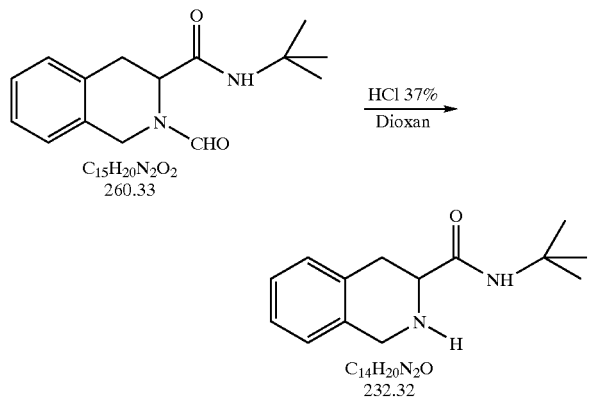

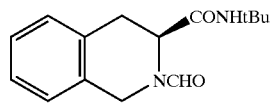

1.4 kg of dioxan and 1.4 kg of H₂O are added to the product obtained in Example 3; 3.3 kg of HCl 36% is poured in slowly at <20° C., it is heated to 25° C. and stirred for 24 h. It is distilled under vacuum at 40° C. until there is a residue and 13 kg of H₂O (and 1.1 kg of acetone) are added. It is stirred for approx. 30 min until the product dissolves, and 0.14 kg of carbon is added. It is stirred for 30 min and filtered on a panel of celite. Then 5 kg of sodium hydroxide at 30% is poured in slowly at room temperature, to pH 9–10. It is stirred for 30 min, cooled to 10° C. for 1 h and filtered on a porous diaphragm; it is then dried in a stove under vacuum at 40° C. 1 kg of (S)-N-tert-butyl-1,2,3,4-tetrahydroisoquinoline-3-carboxamide is obtained (yield 63% of theor.), with HPLC purity of 96%.

What is claimed is:

1. A method of preparation of (S)-N-tert-butyl-1,2,3,4 tetrahydmisoquinoiine-3-carboxamide comprising the following steps:
   a) (3S)-1,2,3,4-tetrahydroisoqulnoline-3-carboxyiic acid is reacted with formic acid to give the compound of formula:

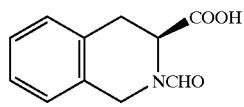

b) the compound thus obtained is reacted with tert-butylamine to give the compound of formula:

the compound thus obtained is then treated with at least one second acid to give (S)-N-tert-butyl-1,2,3.4-tetrahydroisoquinoline-3-carboxamide.

2. A method according to claim 1, wherein step (a) is carried out in toluene.

3. A method according to claim 1, wherein step (a) is carried out in the presence of acetic anhydride.

4. A method according to claim 1, wherein step (a) is carried out at a temperature of 30–70 C.

5. A method according to claim 1, wherein step (b) is carried out in ethyl acetate.

6. A method according to claim 1, wherein step (b) is carried out in the presence of triethylamine and/or ethyl chloroformate.

7. A method according to claim 1, wherein step (b) is carried out at a temperature between −20 and +10° C.

8. A method according to claim 1, wherein step (c) is carried out in dioxan and hydrochloric acid.

9. A method according to claim 1, wherein step (c) is carried out at a temperature between 10 and 40° C.

10. A method according to claim 1, wherein (S)-N-tert-butyl-1,2,3,4-tetra-hydroisoquinoline-3-carboxamide is hydrogenated to give N-tert-butyl-decahydro-(4aS,8aS)-isoquinoline-3(S)-carboxamide.

11. A method according to claim 1, wherein (3S)-1,2.3,4-tetrahydroiso-quinolIne-3-carboxylic acid is obtained by reaction of 1-phenylalanane with formal-dehyde, preferably paraformaldehyde.

12. A method according to claim 4, wherein step (a) is carried out at a temperature of about 50° C.

13. A method according to claim 7, wherein step (b) is carried out at a temperature of about −2° C.

14. A method according to claim 9, wherein step (c) is carried out at a temperature of about 25° C.

* * * * *